US007213288B2

United States Patent
Hohlbein

(10) Patent No.: US 7,213,288 B2
(45) Date of Patent: *May 8, 2007

(54) TOOTHBRUSH

(75) Inventor: Douglas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/089,746

(22) Filed: Mar. 25, 2005

(65) Prior Publication Data

US 2005/0166342 A1 Aug. 4, 2005

Related U.S. Application Data

(63) Continuation of application No. PCT/US03/30633, filed on Sep. 26, 2003.

(60) Provisional application No. 60/414,117, filed on Sep. 27, 2002.

(51) Int. Cl.
A46B 13/02 (2006.01)
A46B 9/04 (2006.01)

(52) U.S. Cl. .......................... 15/22.1; 15/28; 15/167.1; 15/110

(58) Field of Classification Search ............ 15/22.2, 15/22.1, 110, 167.1, 28, 207.2, DIG. 5; D4/104, D4/107, 132, 134
See application file for complete search history.

(56) References Cited

U.S. PATENT DOCUMENTS

| | | | |
|---|---|---|---|
| 411,910 A | 10/1889 | Van Home | |
| 907,842 A | 12/1908 | Meuzies | |
| 1,128,138 A | 2/1915 | Hoffman | |
| 1,142,698 A | 8/1915 | Grove et al. | |
| 1,168,823 A | 6/1916 | Plank | |
| 1,191,556 A | 7/1916 | Blake | |
| 1,268,544 A | 6/1918 | Cates | |
| 1,297,272 A | 3/1919 | Strang et al. | |
| 1,405,279 A | 1/1922 | Cassedy | |
| 1,526,267 A | 2/1925 | Dessau | |
| 1,578,074 A | 3/1926 | Chandler | |
| 1,598,224 A | 8/1926 | Van Stanl | |

(Continued)

FOREIGN PATENT DOCUMENTS

DE 31 14 507 3/1983

(Continued)

OTHER PUBLICATIONS

Top and Side Photographs of head of Reach Max Tooth and Gum Toothbrush.
Sample of Reach Max Tooth and Gum Toothbrush.

*Primary Examiner*—Gary K. Graham
(74) *Attorney, Agent, or Firm*—Ellen K. Park

(57) ABSTRACT

A toothbrush includes a head having a prophylaxis polishing cup closely surrounded by cleaning elements in the form of a bristle ring extending above the upper surface of the cup. Alternatively, the cups could be in the form of arrays of densely packed cleaning elements. The area formed by these configurations retains toothpaste on the toothbrush during use. Additional cleaning elements may be arranged about the periphery of the toothbrush head. The toothbrush may be a powered toothbrush wherein the cups and/or bristle rings rotate, oscillate or reciprocate to better clean teeth.

15 Claims, 3 Drawing Sheets

U.S. PATENT DOCUMENTS

| | | | |
|---|---|---|---|
| 1,852,480 A | 4/1932 | Ruetz | |
| 1,872,832 A | 8/1932 | Silverberg | |
| 1,910,414 A | 5/1933 | Varga | |
| 1,924,152 A | 8/1933 | Coney et al. | |
| 1,993,763 A | 3/1935 | Touchstone | |
| 2,059,914 A | 11/1936 | Rosenberg | |
| 2,083,217 A | 6/1937 | Brothers et al. | |
| 2,088,839 A | 8/1937 | Coney et al. | |
| 2,117,174 A | 5/1938 | Jones | |
| 2,139,245 A | 12/1938 | Ogden | |
| 2,140,307 A * | 12/1938 | Belaschk et al. | 15/28 |
| 2,154,846 A | 4/1939 | Heymann et al. | |
| 2,219,753 A | 10/1940 | Seguin | |
| 2,244,699 A | 6/1941 | Hosey | |
| 2,279,355 A | 4/1942 | Wilensky | |
| 2,305,461 A | 12/1942 | Spyra | |
| 2,312,828 A | 3/1943 | Adamsson | |
| 2,364,204 A * | 12/1944 | Fuller | 601/141 |
| 2,443,461 A | 6/1948 | Kempster | |
| 2,545,814 A | 3/1951 | Kempster | |
| 2,637,870 A | 5/1953 | Cohen | |
| 2,686,325 A | 8/1954 | Silver | |
| 2,702,914 A | 3/1955 | Kittle et al. | |
| 3,103,027 A | 9/1963 | Birch | |
| 3,181,193 A | 5/1965 | Nobles et al. | |
| 3,195,537 A | 7/1965 | Blasi | |
| 3,230,562 A | 1/1966 | Birch | |
| 3,261,354 A | 7/1966 | Shpuntoff | |
| 3,315,296 A | 4/1967 | Richardson | |
| 3,359,588 A | 12/1967 | Kobler | |
| 3,491,396 A | 1/1970 | Eannarino et al. | |
| 3,509,874 A | 5/1970 | Stillman | |
| 3,553,759 A | 1/1971 | Kramer et al. | |
| 3,939,522 A | 2/1976 | Shimizu | |
| 4,128,910 A | 12/1978 | Nakata et al. | |
| 4,277,862 A | 7/1981 | Weideman | |
| D273,635 S | 5/1984 | Stocchi | |
| 4,573,920 A | 3/1986 | d'Argembeau | |
| 4,827,551 A | 5/1989 | Maser et al. | |
| 5,032,082 A | 7/1991 | Herrera | |
| 5,040,260 A | 8/1991 | Michaels | |
| 5,211,494 A | 5/1993 | Baijnath | |
| 5,226,197 A | 7/1993 | Nack et al. | |
| 5,249,327 A | 10/1993 | Hing | |
| 5,335,389 A | 8/1994 | Curtis et al. | |
| 5,341,537 A | 8/1994 | Curtis et al. | |
| 5,353,460 A * | 10/1994 | Bauman | 15/22.1 |
| 5,446,940 A | 9/1995 | Curtis et al. | |
| 5,535,474 A | 7/1996 | Salazar | |
| 5,584,690 A | 12/1996 | Maassarani | |
| 5,604,951 A | 2/1997 | Shipp | |
| 5,625,916 A | 5/1997 | McDougall | |
| 5,628,082 A | 5/1997 | Moskovich | |
| 5,735,011 A | 4/1998 | Asher | |
| 5,784,742 A * | 7/1998 | Giuliani et al. | 15/22.1 |
| 5,799,353 A | 9/1998 | Oishi et al. | |
| 5,802,656 A | 9/1998 | Dawson et al. | |
| 5,806,127 A | 9/1998 | Samoil et al. | |
| RE35,941 E | 11/1998 | Stansbury, Jr. | |
| D402,116 S | 12/1998 | Magloff et al. | |
| D403,510 S | 1/1999 | Menke et al. | |
| 5,873,140 A | 2/1999 | Holloway | |
| 5,896,614 A | 4/1999 | Flewitt | |
| 5,930,860 A | 8/1999 | Shipp | |
| 5,970,564 A | 10/1999 | Inns et al. | |
| 5,974,614 A | 11/1999 | Ross | |
| 5,991,959 A | 11/1999 | Raven et al. | |
| 6,041,467 A | 3/2000 | Roberts et al. | |
| 6,041,468 A | 3/2000 | Chen et al. | |
| D422,143 S | 4/2000 | Beals et al. | |
| D424,808 S | 5/2000 | Beals et al. | |
| D425,306 S | 5/2000 | Beals et al. | |
| 6,058,541 A | 5/2000 | Masterman et al. | |
| 6,067,684 A | 5/2000 | Kweon | |
| 6,098,233 A | 8/2000 | Chen | |
| 6,105,191 A | 8/2000 | Chen et al. | |
| 6,108,851 A | 8/2000 | Bredall et al. | |
| 6,151,745 A | 11/2000 | Roberts et al. | |
| D434,906 S | 12/2000 | Beals et al. | |
| 6,168,434 B1 | 1/2001 | Böhm-Van Diggelen | |
| 6,182,365 B1 | 2/2001 | Tseng et al. | |
| 6,260,227 B1 | 7/2001 | Fulop et al. | |
| 6,276,021 B1 | 8/2001 | Hohlbein | |
| D448,569 S | 10/2001 | Harris et al. | |
| D450,929 S | 11/2001 | Angelini et al. | |
| 6,374,448 B2 | 4/2002 | Seifert | |
| D456,607 S | 5/2002 | Carlucci et al. | |
| 6,421,867 B1 | 7/2002 | Weihrauch | |
| 6,446,295 B1 | 9/2002 | Calabrese | |
| 6,463,619 B2 | 10/2002 | Gavney, Jr. | |
| D465,927 S | 11/2002 | Saindon et al. | |
| D466,303 S | 12/2002 | Saindon et al. | |
| D466,694 S | 12/2002 | Saindon et al. | |
| 6,510,575 B2 | 1/2003 | Calabrese et al. | |
| D469,958 S | 2/2003 | Saindon et al. | |
| 6,513,182 B1 | 2/2003 | Calabrese et al. | |
| 6,571,417 B1 | 6/2003 | Gavney, Jr. | |
| D478,424 S | 8/2003 | Saindon et al. | |
| D480,562 S | 10/2003 | Saindon et al. | |
| 6,665,901 B2 | 12/2003 | Driesen et al. | |
| 6,859,969 B2 | 3/2005 | Gavney et al. | |
| 2001/0023516 A1 | 9/2001 | Driesen et al. | |
| 2002/0004964 A1 | 1/2002 | Luchino et al. | |
| 2002/0029988 A1 | 3/2002 | Blaustein et al. | |
| 2002/0059685 A1 | 5/2002 | Paffrath | |
| 2002/0108194 A1 | 8/2002 | Cartucci et al. | |
| 2002/0124333 A1 | 9/2002 | Hafliger et al. | |
| 2002/0124337 A1 | 9/2002 | Calabrese et al. | |
| 2002/0138926 A1 | 10/2002 | Brown, Jr. et al. | |
| 2002/0138928 A1 | 10/2002 | Calabrese | |
| 2002/0152564 A1 | 10/2002 | Blaustein et al. | |
| 2002/0162180 A1 | 11/2002 | Blaustein et al. | |
| 2003/0033680 A1 | 2/2003 | Davies et al. | |
| 2003/0033682 A1 | 2/2003 | Davies et al. | |
| 2003/0192139 A1 | 10/2003 | Fattori et al. | |
| 2003/0196283 A1 | 10/2003 | Gatzemeyer et al. | |
| 2003/0208865 A1 | 11/2003 | Davies | |
| 2003/0229959 A1 | 12/2003 | Kim et al. | |

FOREIGN PATENT DOCUMENTS

| | | |
|---|---|---|
| EP | 360 766 | 3/1990 |
| EP | 1 308 108 | 5/2003 |
| FR | 2636818 | 9/1988 |
| FR | 2793136 | 5/1999 |
| GB | 388246 | 2/1933 |
| GB | 2040161 | 1/1979 |
| GB | 2371217 | 7/2002 |
| JP | 51 35303 | 8/1976 |
| WO | WO 1998/05241 A | 2/1998 |
| WO | WO 98/18364 | 5/1998 |
| WO | WO 98/22000 | 5/1998 |
| WO | WO 99/37182 | 7/1999 |
| WO | WO 01/01817 | 1/2001 |
| WO | WO 2003/030680 A | 4/2003 |
| WO | WO 2004/019801 A | 3/2004 |

* cited by examiner

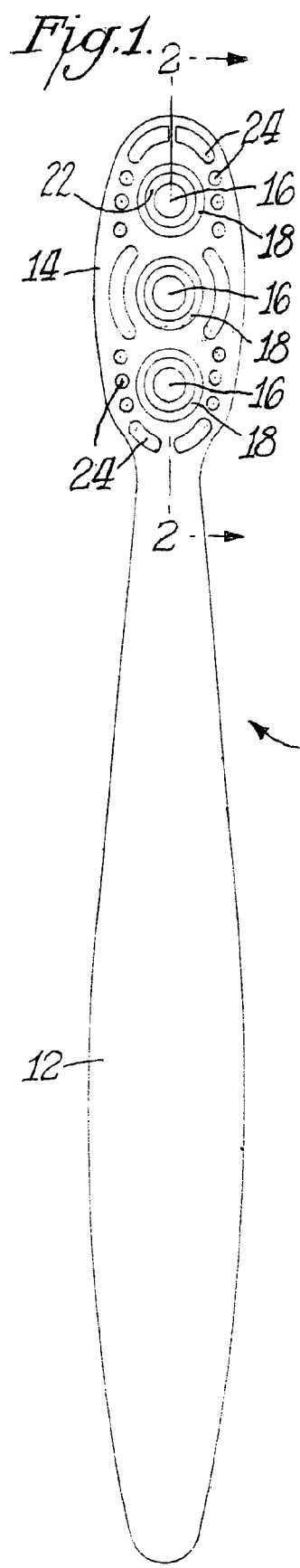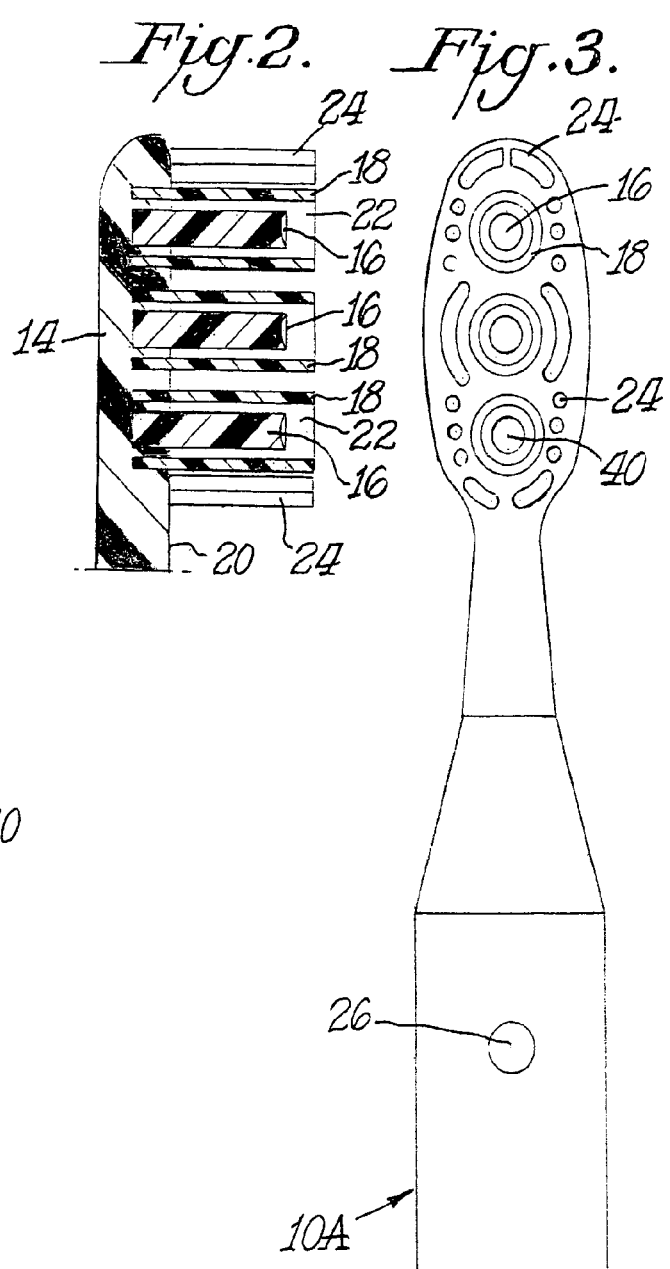

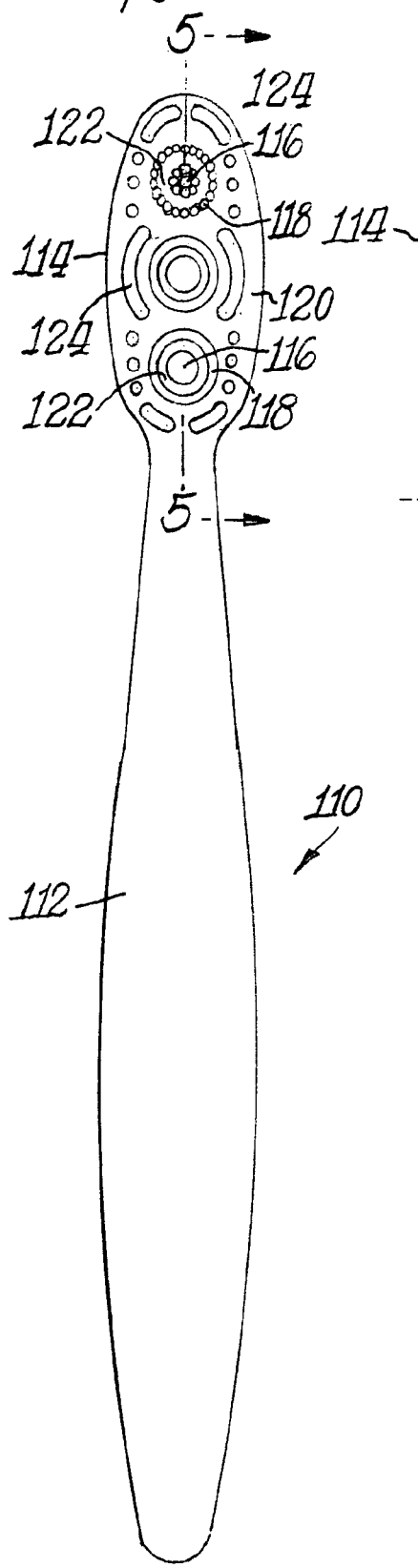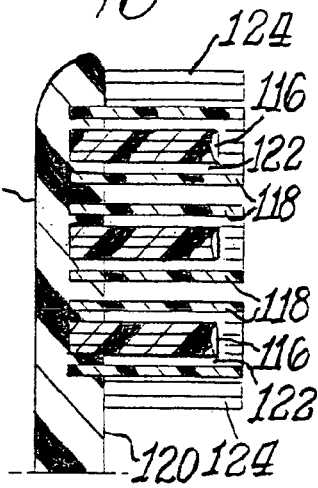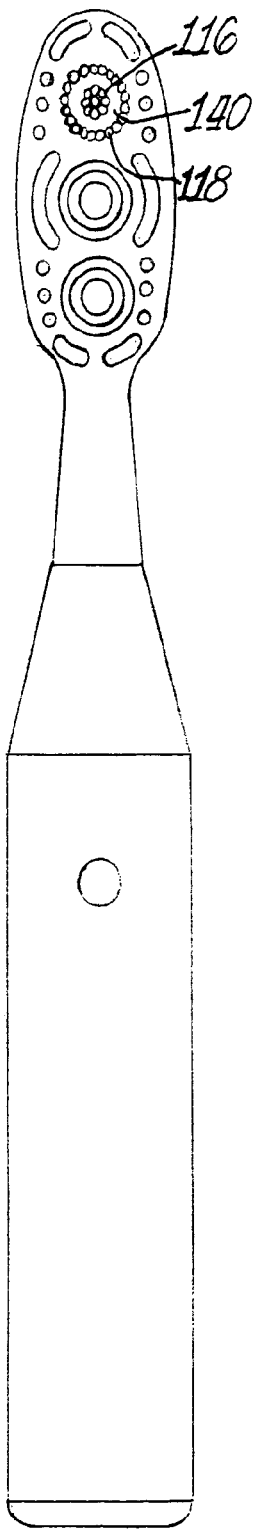

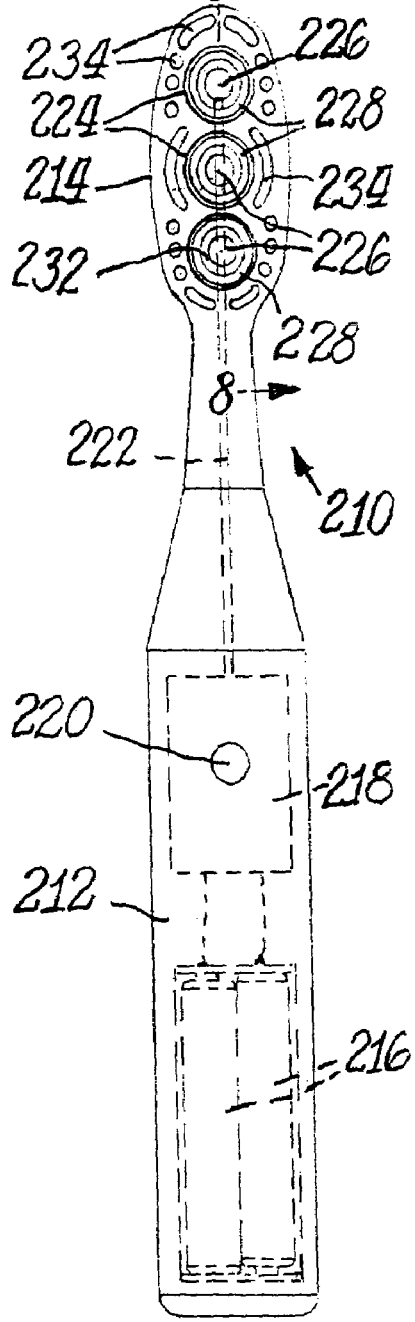
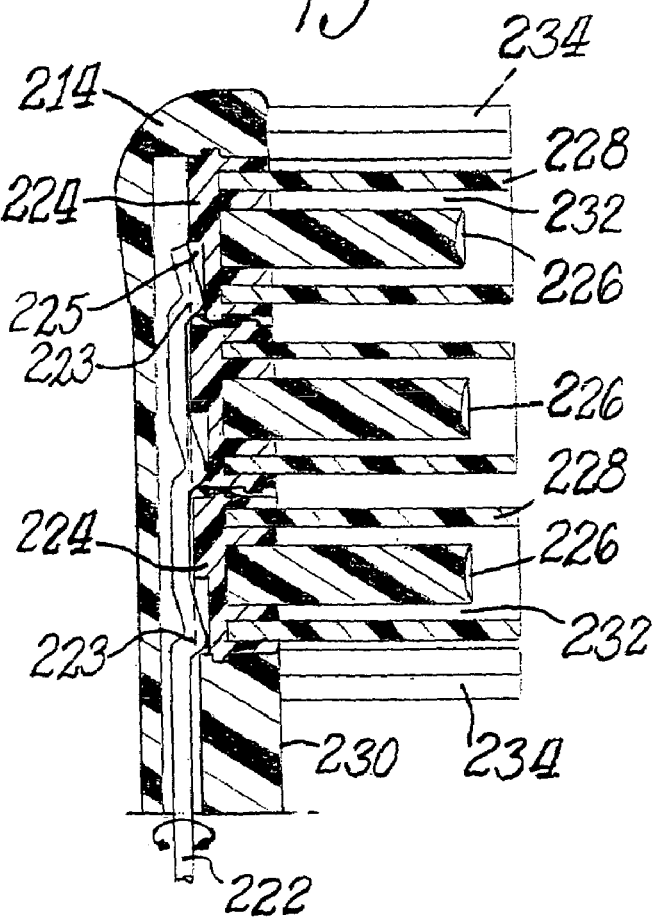

TOOTHBRUSH

This application is a continuation of application PCT/US2003/030633, filed Sep. 26, 2003, which claims the benefit of U.S. Provisional Application 60/414,117 filed Sep. 27, 2002, both of which are incorporated herein by reference in their entirety.

FIELD OF INVENTION

The present invention is directed to a toothbrush, either manual or powered, which includes a handle and a head. Cleaning elements are mounted to the head such as tufts of bristles. When toothpaste is applied to the cleaning elements the user inserts the head into the mouth and brushes the teeth in a known manner. Also included in this invention are prophylaxis polishing cups or arrays of bristles forming cups in the center of the head to hold toothpaste. These cups are closely surrounded by cleaning elements which help to retain the toothpaste within the head.

BACKGROUND OF THE INVENTION

The head of a conventional toothbrush usually has a flat or slightly altered surface to which cleaning elements are attached. Usually the cleaning elements are strands of plastic material(s) formed into tufts, bundles or other groupings. The strands are attached to the head either before or after forming the toothbrush.

Various approaches have been advanced in the prior art for orientating the cleaning elements in the toothbrush.

U.S. Pat. No. 2,083,217 issued Jun. 8, 1937 to E. I. Brothers, et al. discloses two or three circular brush sections which are arranged within cups 5 and 5' that may be screwed into mating receptacles in the tooth brush handle so that they can be removed and replaced as needed (page 2, lines 52–70). Each brush section contains stiff cleaning elements and is spaced from the other along the longitudinal axis of the handle at a distance less than the thickness of a tooth so that the brush operates on both the lingual (inside) and facial (outside) surfaces of the teeth (page 2, column 1, line 71 to column 2, line 9).

U.S. Pat. No. 5,604,951 describes a toothbrush with a head containing a flexible, rubber-like prophylaxis polishing cup or "prophecy cup" similar to that used by dental personnel to professionally clean teeth. This prophy cup is loaded with toothpaste by the user and applied to the teeth. According to this patent, the "soft rubber-like prophy cup device follows the contours of teeth more effectively than bristles" (column 2, lines 23–26). This patent also discloses a ring of cleaning elements ("bristle tufts") placed about the periphery of the toothbrush head which coact with the prophy cups to clean the user's teeth and gums (column 2, lines 34–47).

Another approach to oral hygiene is described in the toothbrush described in U.S. Pat. No. 6,041,468 issued to the assignee of this application. The cleaning elements (bristles) of this toothbrush are arranged in a concave shape across the width of the toothbrush head (See FIGS. 3–5 and column 4, lines 1–22).

Design Patents illustrating circular groups of cleaning elements are U.S. Pat. Nos. Des. 273,635 issued May 1, 1984 to Stocchi and D450,929S issued Nov. 27, 2001 to Angelina, et al.

SUMMARY OF THE INVENTION

This invention seeks to improve the tooth buffing/polishing capability of a toothbrush by inter alia providing a configuration that promotes retention of toothpaste in place within a toothbrush head while in use. This goal is achieved by mounting elastomeric prophy cups on a toothbrush head, which cups are closely surrounded by cleaning elements extending above the surface of the cups.

Unlike a professional dentist's office where the dental professional can repeatedly add toothpaste to a prophy cup, a typical domestic toothbrush user applies but one portion of toothpaste to a toothbrush. A substantial portion of the applied toothpaste, and thus its cleaning power, is typically lost after the first few movements of the toothbrush in the user's mouth. It either falls off as the top of the toothbrush head is tilted from horizontal to vertical as it approaches the mouth or is squeezed off as the toothbrush is pressed against the teeth. The toothpaste is of no cleaning value once it leaves contact with the brush and teeth.

Accordingly, this invention provides a unique combination of features to maintain and retain toothpaste on the head of a toothbrush. Prophy cup(s) are arranged in the center of the toothbrush head, preferably on the longitudinal axis of the head. Alternatively, the cups could be in the form of an array of bristles. These cups are closely surrounded by groupings of cleaning elements that have a greater height relative to the face of the toothbrush head than the height of the prophy cup from that face. This grouping of taller cleaning elements at least partially surrounds the prophy cup to form a barrier around the prophy cup that retains toothpaste when the toothbrush is in use.

An additional set of cleaning elements can then be arranged about the periphery of the toothbrush head to clean the teeth with the toothpaste retained by the prophy cup and surrounding cleaning elements. The outer set of cleaning elements also promotes massaging of the gum and removal of plaque at the gum line.

The cleaning elements are typically bristles secured to the toothbrush head by anchor free tufting (AFT) technology.

The invention may be practiced where each set of cup and surrounding cleaning elements is mounted on a disk and the disk is power driven to rotate continuously in the same direction or back and forth in an oscillating movement.

BRIEF DESCRIPTION OF THE DRAWINGS

This invention is capable of use in a broad array of oral hygiene products. The drawings illustrate one use of the invention and are not to be construed as the only embodiment of the invention.

FIG. 1 is a front elevation view of a toothbrush of this invention showing the arrangement of prophy cups and cleaning elements used in this invention;

FIG. 2 is a cross-sectional view in elevation taken along the line 2—2 of FIG. 1;

FIG. 3 is a front elevation view of a powered toothbrush in accordance with this invention;

FIG. 4 is a front elevation view of a toothbrush showing a further arrangement in accordance with this invention;

FIG. 5 is a cross sectional view in elevation taken along the line 5—5 of FIG. 4;

FIG. 6 is a front elevation view of a powered toothbrush incorporating the cup and cleaning element arrangement of FIGS. 4–5;

FIG. 7 is a front elevation view of a powered toothbrush in accordance with yet another arrangement of this invention; and FIG. 8 is a cross section view in elevation taken along the line 8—8 of FIG. 7.

DETAILED DESCRIPTION OF THE INVENTION

FIG. 1 illustrates a manual toothbrush 10 containing the features of this invention. This toothbrush 10 includes a handle 12 and a head 14. Handle 12 may include a suitable textured grip (not shown) made of elastomeric material. This invention, however, is primarily directed to the arrangement of prophy cups and cleaning elements on head 14.

In accordance with this invention, prophy cups 16 are arrayed in the center of head 14, preferable aligned with the longitudinal axis of toothbrush 10. As illustrated, three prophy cups 16 are affixed to head 14, although use of a larger or smaller number of such cups is contemplated for use with toothbrush 10. The prophy cups 16 are typically made of a soft elastomeric material and, as the name implies, are cup-shaped. The inner surface of the cup can contain ridges which help to clean teeth when the toothbrush is pressed against the user's teeth. More importantly, the cup shape of prophy cups 16 acts to hold toothpaste in place while the toothbrush 10 is in use.

Complementing this function of toothpaste retention is a set of cleaning elements or bristle rings 18 surrounding some or all of the prophy cups 16. As best illustrated in FIG. 2, the bristle rings 18 extend a greater distance above the face 20 of head 14 than the prophy cups 16. This extra height relative to cups 16 acts as a further means for retaining toothpaste within the toothbrush head 14 during use. A preferred placement of the bristle rings 18 is with a space of about one (1) millimeter from the outer circumference of the prophy cup 16.

Upon the user's application of force on the handle 14 as the toothbrush 10 approaches the user's teeth, the toothpaste applied by the user will be forced into the holding areas 22 formed by between a prophy cup 16 and the surrounding bristle ring 18. The toothpaste will be held in holding areas 22 near the top of the bristle rings by the top of prophy cup 16.

This unique combination of prophy cups 16 and closely surrounding bristle rings 18 holds most of the toothpaste exactly where desired, namely, in the area 22 where the principal cleansing components, prophy cup and bristle rings, are in contact with the user's teeth. The surrounding ring of bristles 18 captures the toothpaste as it escapes from the cup 16, to act as a replenishing reservoir when one changes the direction of one's brush stroke.

To complement the cleaning effect of the prophy cups 16 and bristle rings 18, additional elements 24 can be arranged about the periphery of head 14 in a manner similar to that shown in FIGS. 1 and 2. These peripheral cleaning elements 24 help to clean deep between teeth and along the gumline. These additional cleaning elements may be tufts of bristles and may be elastomeric walls or fingers, as illustrated.

Cleaning elements 24 and bristle rings 18 are arranged in both portions of head 14 in a known manner. For example, anchor free tufting (AFT) could be used to mount the cleaning elements. In AFT a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. The term "cleaning elements" is intended to be used in a generic sense which could include conventional fiber bristles or massage elements or other forms of cleaning elements such as elastomeric fingers or walls arranged in a circular cross-section shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

It is to be understood that the specific illustration of the cleaning elements is merely for exemplary purposes. The invention can be practiced with various combinations (such as AFT, etc.) and/or with the same bristle or cleaning element materials (such as nylon bristles, spiral bristles, rubber bristles, etc.) Similarly, while the Figures illustrate the cleaning elements to be generally perpendicular to head 14, some or all of the cleaning elements may be angled at various angles with respect to the face 20 of head 14. It is thereby possible to select the combination of cleaning element configurations, materials and orientations to achieve specific intended results to deliver additional oral health benefits, like enhanced cleaning, tooth polishing, tooth whitening and/or massaging of the gums.

Although the bristle ring 18 is illustrated as being formed by fibrous bristles, the bristle ring could be formed by other types of cleaning elements such as elastomer fingers.

FIG. 3 illustrates a powered version 10A of the toothbrush wherein sections 40 of the head 14 are moved under power or may contain a powered set of cleaning elements. Sections 40 may take the form of circular discs. Preferably, the prophy cups 16 and/or bristle rings 18 would be mounted to the section 40 to be powered to provide rotational or oscillating movement thereto. Switch 26 on toothbrush 10A can be used to activate and deactivate power to the movable elements of toothbrush 10A.

The movable section 40 could be oscillated rotationally such as by using the type of drive mechanism shown in U.S. Pat. No. 5,625,916, or could move in and out using the type of drive mechanism shown in U.S. Pat. No. RE 35,941; all of the details of both patents are incorporated herein by reference thereto. Alternatively, the other types of drives referred to above could move section 40 in other manners and directions. Although FIG. 3 shows movable section 40 to be at one end of the head 14, the movable section(s) would be located at any desired location on the head.

FIGS. 1–3 relate to the practice of the invention wherein the cleaning elements 18 surround prophy cups 16. The invention could, however, be practiced where instead of prophy cups the cups are formed by a dense pack of cleaning elements. This embodiment of the invention is illustrated in FIGS. 4–6. As shown therein the toothbrush 110 has many of the same features as the toothbrush 10. Thus, the toothbrush 110 includes a handle 112 and a head 114 similar to the same components in FIGS. 1–3.

In accordance with the practice of the invention shown in FIGS. 4–6, a central, dense pack of cleaning elements 116 is arrayed in the center of head 114, preferable aligned with the longitudinal axis of toothbrush 110. As illustrated, three circular groups of densely packed cleaning elements 116 are affixed to head 114, although use of a larger or smaller number of such groups is contemplated for use with toothbrush 110. The ends of cleaning element groups 116 are typically contoured in cross-section to provide a cup-like shape. The cup-like shape of cleaning elements 116 acts to hold toothpaste in place while the toothbrush 110 is in use.

Complementing this function of toothpaste retention is a set of cleaning elements or bristle rings 118 surrounding some or all of the cup-shaped cleaning elements 116. As best illustrated in FIG. 5, the bristle rings 118 extend a greater distance above the face 120 of head 114 than the cup-shaped elements 116. This extra height relative to cup-shaped cleaning elements 116 acts as a further means for retaining toothpaste within the toothbrush head 114 during use. A preferred placement of the bristle rings 118 is with a space of about one (1) millimeter from the outer circumference of the cup-shaped elements 116.

Upon the user's application of force on the handle 114 as the toothbrush 110 approaches the user's teeth, the toothpaste applied by the user will be forced into the holding areas 122 formed by the surrounding bristle rings 118. The toothpaste will be held in holding areas 122 near the top of the bristle rings by the top of cup-shaped elements 116.

This unique combination of elements 116 and closely surrounding bristle rings 118 holds most of the toothpaste exactly where desired, namely, in the area 122 adjacent where the principal cleansing components, which are in contact with the user's teeth. The surrounding ring of bristles 118 captures the toothpaste as it escapes from the cup-shaped bristles 116, to act as a replenishing reservoir when one changes the direction of one's brush stroke.

To complement the cleaning effect of the cup-shaped elements 116 and bristle rings 118, additional elements 124 can be arranged about the periphery of head 114 in a manner similar to that shown in FIGS. 4 and 5. These peripheral cleaning elements 124 help to clean deep between teeth and along the gumline.

As with toothbrush 10 of FIGS. 1–2, cleaning elements 116, 118, and 124 are arranged in head 114 in a known manner. Any suitable form of cleaning elements may be used in the broad practice of this invention.

FIG. 6 illustrates a powered version 110A of the toothbrush wherein portions 140 of the head 114 are moved under power or may contain a powered set of cleaning elements. Preferably, the cup-shaped cleaning elements 116 and/or bristle rings 118 would be powered to provide rotational or oscillating movement thereto. A switch 126 on toothbrush 110A can be used to activate and deactivate power to the movable elements of toothbrush 110A. Toothbrush 110A could operate in the same manner as toothbrush 110A.

The toothbrushes 10A and 110A utilize a power drive to move the respective sections 40, 140. FIGS. 7–8 illustrate in greater detail one such practice of the invention. As shown in FIG. 7, a powered toothbrush 210 includes a handle 212 and a head 214. Handle 212 includes a battery pack or rechargeable unit 216 which provides the motive power to toothbrush 210. This power source 216 is electrically connected to motor 218 by suitable wiring or after connection. Selective operation of motor 218 is controlled by switch 220.

Extending from one end of motor 218 toward head 214 is drive shaft 222. Motor 218 can be geared to impart rotational or reciprocating motion to drive shaft 222. The other end underlies the discs or movable platforms 224 on which are mounted cups 226 and taller cleaning elements 228.

In the embodiment illustrated in FIGS. 7 and 8, the drive shaft rotates back and forth through an angle of about 60–90° as illustrated in FIG. 8. Offsets 223 in drive shaft 222 rotate a similar angular distance. These offsets 223 in drive shaft 222 are positioned in slots 225 formed in the base of platforms 224. As the shaft rotates back and forth through the aforesaid angle, offsets 223 cause reciprocation of platforms 224 as the offsets alternatively push the sides of slots 225 in one direction and then another. This, in turn, causes reciprocating movement of cups 226 or bristles 228, depending upon which is mounted on platform 224. That movement aids in cleaning of teeth and invigoration of gums.

In accordance with this invention, cups 226 are mounted on platforms 224 in the center of head 214, preferably aligned with the longitudinal axis of toothbrush 210. As illustrated, three cups 226 are contained in head 214, although use of a larger or smaller number of such cups is contemplated for use with toothbrush 210. Where cups 226 are prophy cups, the prophy cups 226 are typically made of a soft elastomeric material and, as the name implies, are cup-shaped. The inner surface of the cup can contain ridges which help to clean teeth when the toothbrush is pressed against the user's teeth. Also, the cup shape of prophy cups 226 acts to hold toothpaste in place while the powered toothbrush 10 is in use.

Although prophy cups are specifically illustrated, cups 226 could also be densely packed cleaning elements, such as cups 116.

Complementing these functions of toothpaste retention and cleaning is a set of cleaning elements or bristle rings 228 surrounding some or all of the cups 226, as previously described with respect to toothbrushes 10 and 110.

It is to be understood that various features shown in an individual embodiment may be incorporated in other embodiments. Thus, for example, where a toothbrush utilizes a plurality of cups all of the cups may be prophy cups or all of the cups may be cups formed by densely packed cleaning elements. Alternatively, a combination of the two different types of cups may be used in any suitable arrangement. Thus, where three cups are used the end cups may be of one type which differs from the central cup or only one of the end cups may differ from the other cups. Where more than three cups are used the cups are preferably longitudinally aligned and could be all or a combination of the different types of cups. Alternatively, where the plurality of cups are used if a wider toothbrush head is used the cups need not be longitudinally aligned. Although the sets of cups and bristle rings are illustrated as being uniformly spaced from each other, a non-uniform spacing could be used.

What is claimed is:

1. A toothbrush comprising a handle, a head attached to the handle, a power source for imparting movement to the head, the head having a face on which is located a plurality of outwardly extending cups, each cup defined by a central, densely packed plurality of first cleaning elements having a first center and surrounded by a ring of second cleaning elements having a second center, at least one of the cups being surrounded by a plurality of third cleaning elements having a third center and arcuately arranged on opposite sides of the at least one cup, the first, second and third centers being generally concentric.

2. The toothbrush of claim 1, wherein additional cleaning elements are arranged about at least part of the periphery of the toothbrush head to form a substantially closed loop of cleaning elements around the periphery.

3. The toothbrush of claim 2 wherein the additional cleaning elements are defined by a plurality of cleaning element segments that only partially surround each cup.

4. The toothbrush of claim 1 wherein the ring of second cleaning elements completely surrounds the plurality of first cleaning elements.

5. The toothbrush of claim 4 wherein the inner circumference of the ring of second cleaning elements is located about 1 millimeter from the outer circumference of the plurality of first cleaning elements.

6. The toothbrush of claim 1 wherein the second cleaning elements are elastomeric.

7. The toothbrush of claim 6 wherein the second cleaning elements further comprise elastomeric wails.

8. The toothbrush of claim 7 further comprising a plurality of additional cleaning elements arranged by anchor free tufting on the head.

9. The toothbrush of claim 8 wherein the additional cleaning elements are disposed along an outer edge of the head opposite the handle.

10. The toothbrush of claim 9 wherein the additional cleaning elements are additionally disposed along an edge of the head adjacent the handle.

11. The toothbrush of claim 1 wherein the plurality of cups are uniformly spaced and longitudinally aligned along the longitudinal axis of the head.

12. The toothbrush of claim 1 further comprising a plurality of additional cleaning elements that only partially surround each cup.

13. The toothbrush of claim 12 wherein each plurality of additional cleaning elements has a center that is generally concentric with the first and second centers.

14. The toothbrush of claim 13 wherein the plurality of additional cleaning elements are arcuately arranged along opposite ends of the longitudinal axis of the head.

15. The toothbrush of claim 1 wherein the ring of second cleaning elements extends a distance above the face of the head greater than the height of the first cleaning elements.

* * * * *